US006552066B1

(12) United States Patent
Sharpe et al.

(10) Patent No.: US 6,552,066 B1
(45) Date of Patent: Apr. 22, 2003

(54) PROTEIN TYROSINE KINASE INHIBITORS FOR TREATING OSTEOARTHRITIS

(76) Inventors: Thomas R. Sharpe, 112 W. Pembrey Dr., Wilmington, DE (US) 19803; George W. Vasios, 195 Winthrop Rd., No. 1, Brookline, MA (US) 02146; R. Nelson Campbell, 7620 Old Georgetown Rd., Unit #1023, Bethesda, MD (US) 20814

( * ) Notice: Subject to any disclaimer, the term of this patent is extended or adjusted under 35 U.S.C. 154(b) by 0 days.

(21) Appl. No.: 09/038,187

(22) Filed: Mar. 10, 1998

Related U.S. Application Data

(63) Continuation of application No. PCT/US96/14491, filed on Sep. 11, 1996, which is a continuation-in-part of application No. 08/526,290, filed on Sep. 11, 1995, now abandoned.

(51) Int. Cl.$^7$ .................... A61K 31/40; A61K 31/275
(52) U.S. Cl. .................... 514/419; 514/520; 514/523
(58) Field of Search .................. 514/419, 520, 514/523

(56) References Cited

U.S. PATENT DOCUMENTS

| 5,591,740 A | 1/1997 | Chipman et al. ........... 514/215 |
| 5,658,756 A | 8/1997 | Rodan et al. ............... 435/69.1 |
| 5,889,003 A | * 3/1999 | Dhainaut et al. ......... 514/233.5 |

FOREIGN PATENT DOCUMENTS

| EP | 0 551 849 A1 | 7/1993 |
| EP | 0 633 022 | 1/1995 |
| GB | 2 262 524 | 6/1993 |
| JP | 04046120 | 2/1992 |
| WO | WO92/00999 | 1/1992 |
| WO | WO 92/16517 | 10/1992 |
| WO | WO 93/05014 | 3/1993 |
| WO | WO 93/16703 | 9/1993 |
| WO | WO 93/18173 | 9/1993 |
| WO | WO95/02420 | 1/1995 |
| WO | WO 95/05824 | 3/1995 |
| WO | WO95/14464 | 6/1995 |

OTHER PUBLICATIONS

Trinks, U.,et al., "Dianilinophthalimides: Potent and Selective, ATP–Competitive Inhibitors of the EGF–Receptor Protein Tyrosine Kinase," *J. Med. Chem.*, 37:1015–1027 (1994).

Rewcastle, G.W.,et al., "Tyrosine Kinase Inhibitors. 5. Synthesis and Structure–Activity Relationships for 4–[(Phenylmethyl)amino]– and 4–(Phenylamino) Quinazolines as Potent Adenosine 5'—Triphosphate Binding Site Inhibitors of the Tyrosine Kinase Domain of the Epidermal Growth Factor Receptor," *J. Med. Chem.*, 38:3482–3487 (1995).

Maguire, M.P.,et al., "A New Series of PDGF Receptor Tyrosine Kinase Inhibitors: 3–Substituted Quinoline Derivatives," J. Med. Chem., 37: 2129–2137 (1994).

Burke, T.R.,et al., "Bicyclic Compounds as Ring–Constrained Inhibitors of Protein–Tyrosine Kinase P56$^{lck1}$," *J. Med. Chem.*, 36:425–432(1993).

Yoneda, T.,et al., "Herbimycin A, a PP60$^{C-SRC}$ Tyrosine Kinase Inhibitor, Inhibits Osteoclastic Bone Resorption In Vitro and Hypercalcemia in Vivo," J. Clin. Invest., 91:2791–2795(1993).

Levitzki A.,et al., "Tyrosine Kinase Inhibition: An Approach to Drug Development," Science, 267:1782–1788(1995).

Geng, Y., and Lotz, M., "Tyrosine Kinase Signaling Pathways in IL–1 Activation of Chondrocytes," *Arthritis and Rheumatism, 38* (9 Suppl): S 389 (Sep. 21, 1995).

Lotz, M. and Geng, Y., "Signaling Pathways Involved with the Expression of Inducible Nitric Oxide Synthase in Human Articular Chondrocytes," *FASEB Journal, 8(4)*: A365 (Mar. 15, 1994).

Geng, Y. et al. "Activation of ERK, JNK and P38–MPK2 by IL–1 and TNF in Human Articular Chondrocytes," *FASEB Journal, 10(6)*: A 1324 (Apr. 30, 1996).

Geng, Y. et al., "Regulation of Cyclooxygenase II Expression in Articular Chondrocytes," *FASEB Journal, 9(3)*: A 532 (Mar. 9, 1995).

Geng, Y. et al., "Tryosine Kinases Are Involved with the Expression of Inducible Nitric Oxide Synthase in Human Articular Chondrocytes," *Journal of Cellular Physiology, 163(3)*: 545–554 (Jun. 1995).

Geng, Y. et al., "Regulation of Cyclooxygenase–2 Expression in Normal Human Articular Chondrocytes," *Journal of Immunology,* 155: 796–801 (1995).

Conquer, J.A. et al., "Orthovanadate Inhibits Interleukin–1 and Phorbol Ester Induced Collagenase Production by Chondrocytes," *Annals NY Academy of Sciences, 732*: 447–449 (1994).

Cuzzocrea, S., et al., "The Tyrosine Kinase Inhibitor Tyrphostin AG126 Reduces the Development of Acute and Chronic Inflammation," *American J. of Pathology, 157(1)*: 145–148 (2000).

Mitchell, P.G. and Cheung, H.S., "Protein Kinase Regulation of Tumor Necrosis Factor Alpha Stimulated Collagenase and Stromelysin Message Levels in Chondrocytes", *Biochemical and Biophysical Research Communications, 196(3)*:1133–1142 (Nov. 15, 1993).

Cruz, T. F., et al., "Inverse Correlation Between Tyrosine Phosphorylation and Collagenase Production in Chondrocytes," *Biochem., J., 269*:17–721 (1990).

(List continued on next page.)

Primary Examiner—Theodore J. Criares
(74) *Attorney, Agent, or Firm*—Hamilton, Brook, Smith and Reynolds, P.C.

(57) ABSTRACT

Disclosed is a method of treating an individual or animal with osteoarthritis. The method comprises administering to the individual or animal a therapeutically effective amount of a protein tyrosine kinase inhibitor.

14 Claims, No Drawings

OTHER PUBLICATIONS

Richard, M., et al., "Calmodulin–Dependent Collagenase and Proteoglycanase Activities in Chondrocytes from Human Osteoarthritic Cartilage," *Biochemical and Biophysical Research Communications, 174(3)*:1204–1207 (Feb. 14, 1991).

Xie, D., et al, Cartilage Chondrolysis by Fibronectin Fragments is Associated with Release of Several Proteinases: Stromelysin Plays a Major Role in Chondrolysis,*Archives of Biochemistry and Biophysics, 311(2)*:205–212 (Jun. 1994).

Geng, Y., et al., "Regulation of Cyclooxygenase–2 Expression in Normal Human Articular Chondrocytes," *The Journal of Immunology*, 155:796–801 (1995).

Hanglow, A.C., "Pulmonary–Allergy, Gastrointestinal, Dermatological & Arthritis Osteoarthritis: Clinical, Biochemical and Molecular Aspects of Cartilage Degradation," *Exp. Opin. Invest. Drugs* 4(3):253–256 (1995).

Niebes, P., et al., "Effect of Drugs on Collagen Fibrillation and Collagen Degradation In Vitro," *European Journal of Rheumatology and Inflammation, 2(2)*:226–229 (1979).

Chaudhary, L.R., et al., "Regulation of Interleukin–8 Gene Expression by Interleukin–1β, Osteotropic Hormones, and Protein Kinase Inhibitors in Normal Human Bone Marrow Stromal Cells," *the Journal of Biological Chemistry, 271(28)*:16591–16596 (1996).

Xie, B., et al., "Regulatory Mechanisms for the Expression of Type IV Collagenases/Gelatinases in Murine Macrophages," *Journal of Immunology, 152*:3637 (1994).

Racewicz, A. et al., "Are Nonsteroidal Antiiflammatory Drugs Necessary in Treatment of Osteoarthritis," *Reumatologia, T. XXXIV, 2–3*, pps. 384–389 (1996).

* cited by examiner

PROTEIN TYROSINE KINASE INHIBITORS FOR TREATING OSTEOARTHRITIS

RELATED APPLICATIONS

This application claims priority to and is a continuation of International Application No. PCT/US96/14491, filed on Sep. 11, 1996, which is a continuation-in-part of U.S. Ser. No. 08/526,290, filed Sep. 11, 1995, now abandoned, the entire teachings of which are incorporated herein by reference.

BACKGROUND

Osteoarthritis or degenerative joint disease is a slowly progressive, irreversible, often monoarticular disease characterized by pain and loss of function (Mankin and Brandt, Pathogenesis of Osteoarthritis in "Textbook of Rheumatology", Kelly, et al., (eds.) 3rd edition, W. B. Saunders Co., Philadelphia, pp.14699–111471) and Dean, Arth. Rheum. 20 (Suppl. 2):2 (1991)). The underlying cause of the pain and debilitation is the cartilage degradation that occurs as a result of the disease. A typical end-stage clinical picture includes complete erosion of the weight-bearing articular cartilage, requiring total joint replacement.

A class of inhibitors of protein kinase C are hymenialdisines and hymenialdisine analogues (Nambi et al., WO 93/16703). For example, debromohymenialdisine, inhibits protein kinase C gamma (108% at 100 $\mu$m), protein kinase C alpha (97% at 100 $\mu$m), protein kinase C beta (95% at 100 $\mu$m), as well as $Ca^{2+}$-calmodulin dependent protein kinase II, (94% a 100 $\mu$m). Hymenialdisine and hymenialdisine analogues contain a pyrroloazepine ring system, shown below, along with a numbering system for the ring atoms:

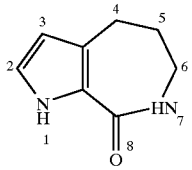

Analogues of hymenialdisine also have a five membered, nitrogen-containing heterocyclic ring which is bonded to the four position of the pyrroloazepine ring system. Examples of hymenialdisines and analogues thereof which have been shown to inhibit cartilage degradation in the bovine cartilage explant assay include Z-debromohymenialdisine, E-debromohymenialdisine and Z-hymenialdisine (Experientia., 44:86 (1988) and Pettit, et al., Can. J. Chem., 68:1621 (990).

Z-hymenialdisine or Z-debromohymenialdisine are represented by the formula:

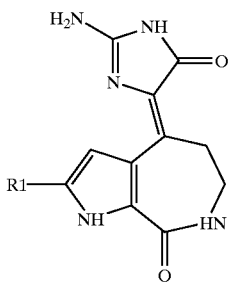

R1 = Br or H

Z-debromohymenialdisine also slows the progression of osteoarthritis in animals. The use of hymenialdisines and analogues thereof for the treatment of osteoarthritis is disclosed in Chipman and Faulkner, U.S. Ser. No. 08/472,902 filed Jun. 7, 1995, now U.S. Pat. No. 5,591,740, issued on Jan. 7, 1997, the entire teachings of which are incorporated herein by reference.

Currently, other than the hymenialdisines and analogues thereof, discussed above, there is no known, demonstrated therapeutic approach available that will slow the clinical progression of osteoarthritis, although steroids and non-steroidal anti-inflammatory drugs are used to ameliorate the pain and inflammation associated with the disease. Consequently, there is a need for new therapeutics which slow the joint degeneration caused by osteoarthritis.

SUMMARY OF THE INVENTION

It has now been found that tyrosine kinase inhibitors significantly reduce or prevent cartilage degradation in chondrocytes. Specifically, the tyrosine kinase inhibitors genistein, herbimycin A, 4,5-dianilinophthalimide (DAPH), tyrphostin AG 82 and tyrphostin AG 556 slow interleukin-1 (IL-1) induced degradation of extracellular matrix by chondrocytes in cell culture (Examples 1 and 7). Herbimycin A and tyrphostin AG 82 also reduce cartilage degradation in a bovine cartilage explant assay (Examples 2 and 3). Protein tyrosine kinase inhibitors have also been shown to inhibit IL-1 induced increases in stromelysin mRNA levels (Example 4) and IL-1 induced increases in prostromelysin protein levels (Example 5). Based on these discoveries, methods of treating individuals with osteoarthritis and methods of inhibiting cartilage degradation in individuals are disclosed.

One embodiment of the present invention is a method of treating an individual or animal with osteoarthritis. The method comprises administering a therapeutically effective amount of a protein tyrosine kinase inhibitor to the individual or animal. Another embodiment of the present invention is a method of inhibiting or preventing cartilage degradation in an individual or animal. The method comprises administering a therapeutically effective amount of a tyrosine kinase inhibitor to the individual or animal.

The disclosed method of treatment inhibits the cartilage degradation associated with the osteoarthritis. Treatments presently used for osteoarthritis only alleviate the symptoms of the disease, for example the pain and inflammation that result from joint deterioration. Therefore, the disclosed treatment for osteoarthritis has the advantage over presently used methods of treatment in that the disclosed method can slow or arrest the progression of the disease rather than merely alleviate its symptoms.

DETAILED DESCRIPTION OF THE INVENTION

Protein tyrosine kinases (PTKs) occur as membrane-bound receptors or cytoplasmic proteins. They are involved in regulating a wide variety of cellular functions, including cytokine responses, antigen-dependent immune responses, cellular transformation by RNA viruses, oncogenesis, cell cycle, and modification of cell morphology. PTKs regulate these functions by activating, directly or indirectly, intracellular signalling pathways, including Ras, phosphatidylinositol 3 kinase (PI3K), phospholipase C-$\gamma$ (PLC-$\gamma$) and mitogen-activated pathway (MAP). It has now been found that PTKs also regulate cellular functions which result in the cartilage degradation associated with osteoarthritis.

Activation of PTKs results in auto-phosphorylation of a tyrosine residue in the protein tyrosine kinase. Autophosphorylation of PTKs facilitates the interaction of protein substrates with the active site and results in the phosphorylation of tyrosine residues in the protein substrates. Protein substrates of PTKs are generally cytosolic signalling molecules whose function is turned off or on as a result of phosphorylation. Activation of protein substrates by PTKs can cause a cascade of intracellular reactions resulting in the activation of other proteins or previously unexpressed or underexpressed genes. This cascade of events is referred to as a signalling pathway, which regulates cellular functions, including the cellular functions discussed above.

Because PTKs regulate cellular functions which cause the cartilage degradation associated which osteoarthritis, the progression of the disease can be slowed or arrested by inhibiting PTKs. As used herein, "inhibiting a PTK" refers to blocking the signal transduction pathway whereby an activated PTK regulates a cellular function. In the present invention, a PTK inhibitor is used which blocks a signal transduction pathway in which an activated PTK regulates one or more cellular functions which result in cartilage degradation. Included are PTK inhibitors which reduce cartilage degradation in IL-1 activated chondrocytes in cell culture, which downregulate matrix metalloproteinase (MMP) and/or aggrecanase mRNA levels in IL-1 activated chondrocytes in cell culture or which downregulate MMP and/or aggrecanase protein levels in chondrocytes in cell culture.

A PTK inhibitor includes a small organic molecule or polypeptide which blocks a PTK regulated signaling pathway, as discussed above. As used herein, a PTK inhibitor can act by a number of different mechanisms. Preferably, the PTK inhibitor can act by inhibiting the initial autophosphorylation event, discussed above. Alternatively, the PTK inhibitor can act by inhibiting the phosphorylation of the protein substrate, for example, by competing with the protein substrate or ATP for binding with the PTK. A PTK can also act by more than one of these mechanisms.

As used herein, a PTK inhibitor can act by other mechanisms. For example, compounds which prevent binding of activating molecules (e.g. growth factors) to receptor PTKs, either by blocking the receptor (e.g. a receptor antagonist) or by binding with the activating molecule itself. Alternatively, a PTK inhibitor can act by blocking one of the biochemical reactions in the cascade of reactions initiated by activation of the PTK. For example, as noted above, activation of a PTK can result in the activation of the Ras, phosphatidylinositol 3 kinase (PI3K), phospholipase C-γ (PLCγ) and mitogen-activated pathway (MAP). Agents which can block any one of these pathways following their initiation by PTK activation can also downregulate cellular functions controlled by the respective PTK.

PTK inhibitors suitable for use in the method of treatments disclosed herein include PTK inhibitors which are natural products. Examples include quercetin, genistein, lavendustin A, erbstatin, herbimycin A, rapamycin, piceatannol and lavendustin B. The chemical structures of these compounds are provided in the 1995 CALBIOCHEM® Signal Transduction Catalog, (pages 143–153) (hereinafter the "CALBIOCHEM® Catalog").

PTK inhibitors suitable for use in the method of treatments disclosed herein also include synthetic PTK inhibitors. Synthetic PTK inhibitors are disclosed in the 1995 CALBIOCHEM® Catalog (pages 143–153) and in Levitzki and Gazit, Science 267:1782 (1995).

In one embodiment, the synthetic PTK inhibitor used in the method of treatment comprises a compound represented by Structural Formula (I):

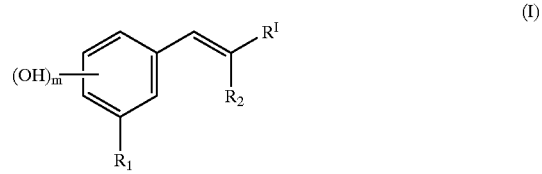

wherein m is one or two; $R_1$ is —H, —OH or —OMe; $R_2$ is —H or —CN; and $R'$ is —H, —NO$_2$, halogen or an organic radical chosen such that the compound represented by Structural Formula (I) inhibits PTKs. Examples of suitable organic radicals include —CN, —CO—NH$_2$, —CS—NH$_2$, —CO—NHR$^{10}$, —CS—NHR$^{10}$, phenyl, substituted phenyl, substituted heteroaryl and heteroaryl (e.g. pyrimidyl, pyridinyl). Suitable substituents for a substituted alkyl or alkenyl group include —NH$_2$, —NO$_2$, halogen, —CN, —CO—NH$_2$, —CS—NH$_2$, —CO—NHR$^{10}$, —CS—NHR$^{10}$, phenyl substituted phenyl, substituted heteroaryl and heteroaryl. $R^{10}$ is a substituted or unsubstituted C1 to about C8 straight or branched chain alkyl or alkenyl group. Suitable substituents for a phenyl or heteroaryl group include halogen, —NO$_2$, —CN and C1–C4 straight or branched chain alkyl. A substituted phenyl, alkyl or alkenyl group can have more than one substituent.

Examples of compounds represented by Structural Formula (I) include dihydroxynitrostyrenetyrphostin AG18, tyrphostin AG82, tyrphostin AG99, tyrphostin AG213, tyrphostin AG308, tyrphostin AG494, tyrphostin AG555, 3,4-dihydroxy-cis-cinnamonitrile, tyrphostin AG825, tyrphostin AG765, tyrphostin A48, tyrphostin A51, tyrphostin B42, tyrphostin B44(−), tyrphostin B46, tyrphostin B48, tyrphostin B50(+) and tyrphostin B56. The structures of these compounds are disclosed in Levitzki and Gazit and/or in the 1995 CALBIOCHEM® Catalog on pages 143–153. Preferably, the PTK inhibitor,represented by Structural Formula (I) comprises a 3,4-dihydroxy-cis-cinnamonitrile moiety, i.e., m is 2, $R_1$ is —H and $R_2$ is —CN.

In another embodiment, the synthetic PTK inhibitor used in the method of treatment comprises a dianilinophthalimide moiety represented by Structural Formula (II):

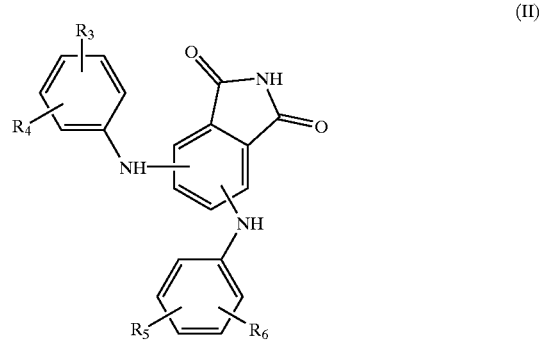

wherein $R_3$–$R_6$ are each independently selected from the group consisting of —H, —Cl, —OH and —OMe. Examples includes 3,4-dianilinophthalimide and 2,5-dianilinophthalimide. The structure of these compounds are disclosed in Levitzki and Gazit.

In another embodiment, the synthetic PTK inhibitor used in the methods of treatment disclosed herein is a compound which comprises a quinoline moiety or an isoquinoline moiety and is represented by Structural Formula (III):

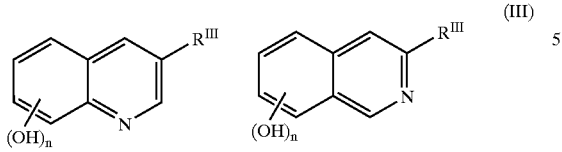

wherein n is one, two or three; $R^{III}$ is an organic radical chosen such that the compound represented by Structural Formula (III) inhibits PTKs. Examples of suitable organic radicals include —CO—NH$_2$, —CS—NH$_2$, —CO—NHR$^{10}$, —CS—NHR$^{10}$, substituted alkyl and substituted alkenyl. $R^{10}$, substituted alkyl and substituted alkenyl are as defined above for Structural Formula (I). Examples of compounds which are PTK inhibitors and which comprise an isoqunioline moiety include compounds represented by Structural Formula (IV):

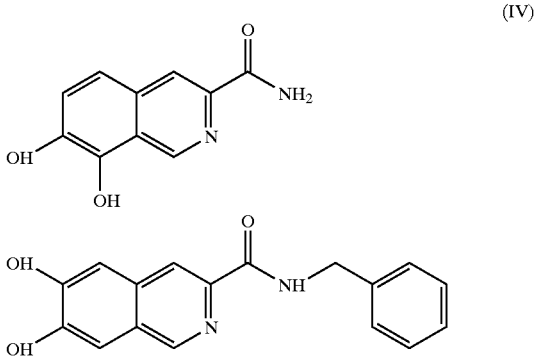

In another embodiment, the synthetic PTK inhibitor used in the method of treatment is a compound comprising a quinazoline moiety and is represented by Structural Formula (V):

wherein n is one, two or three; $R^V$ is an organic radical chosen so that the compound represented by Structural Formula (V) is a PTK inhibitor. $R^V$ can be, for example, —NHR$^{11}$, —OR$^{11}$, SR$^{11}$, wherein $R^V$ is a phenyl group, substituted phenyl group, substituted heteroaryl group or heteroaryl group (e.g. pyrimidyl or pyridinyl) optionally substituted with one or more substituents selected from the group consisting of halogen, —OH, —OMe, —NH$_2$, —CN and —NO$_2$. Tyrphostin AG1478 is one example of a compound represented by Structural Formula (V). The structure of this compound is disclosed in Levitzki and Gazit. See also Barker, European Patent Application 0520722 (1992), Fry et al., Science 265:1093 (1994), and Osherov and Levitizki, Eur. J Biochem. 225:1047 (1994). The entire teachings of these references are incorporated by reference into this application.

In another embodiment, the synthetic PTK inhibitor used in the method of treatment is a compound comprising a flavone or isoflavone moiety and is represented by Structural Formula (VI):

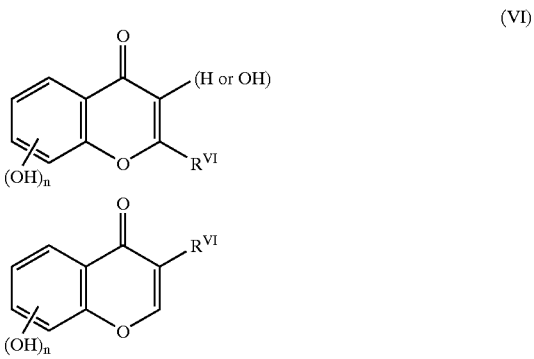

wherein n is one, two or three; $R^{VI}$ is an organic radical chosen so that the compound represented by Structural Formula (VI) is a PTK inhibitor. $R^{VI}$ can be, for example, a phenyl group or heteroaryl group (e.g. pyrimidyl or pyridinyl) substituted with one or more substituents selected from the group consisting of halogen, —OH, —OMe, —NH$_2$, —CN and —NO$_2$. Aminogenistein is one example of a PTK inhibitor represented by Structural Formula (VI). The structure of this compound is disclosed in the 1995 CALBIOCHEM® Catalog.

In another embodiment, the PTK inhibitor is represented by Structural Formula (VII):

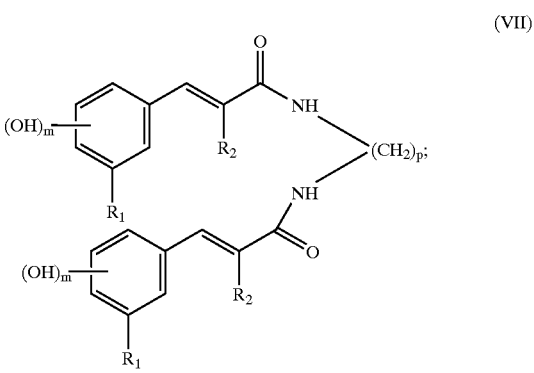

wherein m, $R_1$ and $R_2$ are as described above for Structural Formula (I); p is an integer from one to about eight, preferably from one to about four.

In another embodiment the PTK inhibitor is a tryphostin. Tryphostins are defined in Mazunder et al., Biochemistry 34:15111 (1995), the entire teachings of which are incorporated into this application by reference.

Other examples of PTK inhibitors include tyrphostin AG10, tyrphostin AG17, tyrphostin AG825, tyrphostin AG789, tyrphostin AG1112, tyrphostin AG 370, tyrphostin AG 879, Bis-tyrphostin, 5-amino-N-(2,5-dihydroxybenzyl) methyl salicylate, 2,5-dihydroxymethylcinnamate, HNMPA-(AM)$_3$, RG-13022, RG-14620 and ST638. Compounds which inhibit the catalytic site of tyrosine kinases include the Ca$^{2+}$, antagonists chlorpromazine, imipramine and dibucaine (End et al., Res. Commun. Chem. Pathol. Pharmacol. 107:670 (1987), flavanoids (Hagiwara et al., Biochem. Pharmacol. 37:2987 (1987), 4-hydroxycinnamides (Shiraishi et al., Biochem. Biophys. Res. Commun. 147:322 (1987) and α-cyanocinnamides (Shiraishi et al., Chem. Pharm Bull. 36:974 (1988). For structures of these compounds, see also Levitzki and Gazit or the 1995 CALBIOCHEM® Catalog.

It is to be understood that many modifications to the Structural Formulas I–VII and to the compounds listed above can be made which result in analogs which are also PTK inhibitors. Such modifications include replacing a phenolic hydroxyl group with an —H, a lower alkyl group (e.g., a C1–C4 straight or branched chain alkyl group), —Cl, —OCH$_3$, or —NH$_2$ or adding a —Cl, —OCH$_3$ or —NH$_2$ group to a phenol or resorcinol ring. Analogs such as those described above are included within the meaning of the term "PTK inhibitor", and can be identified by in vitro assays by their ability, for example, to inhibit IL-1 stimulated cartilage degradation in chondrocytes in culture, for example the assay described in Example 1.

The method of the present invention can be used to treat individuals, i.e. humans, or animals with osteoarthritis. It can also be used to slow or prevent cartilage degradation in individuals or animals with a condition which causes cartilage degradation. Animals which can be treated with the method include dogs, cats, guinea pigs, horses, farm animals and the like.

A "therapeutically effect amount" of a protein tyrosine kinase inhibitor is the quantity of inhibitor which, after being administered to an individual or animal with osteoarthritis, brings about an amelioration of the disease processes associated with osteoarthritis without causing unacceptable side-effects. "Ameliorating the disease processes associated with osteoarthritis" can include lowering the amount of active matrix metalloproteinase in the individual, e.g. by inhibiting a matrix metalloproteinase, by preventing transcription of a gene which encodes a matrix metalloproteinase, by preventing the synthesis and/or secretion of a matrix metalloproteinase or by preventing interleukin-1 upregulation of matrix metalloproteinase activity. Alternatively, it can also include slowing, arresting or reversing the degradation and loss of function typically observed in a joint afflicted with osteoarthritis, e.g. by reducing the rate of cartilage degradation in the joint. "Ameliorating the disease processes associated with osteoarthritis" can also include a lessening of the pain and inflammation associated with osteoarthritis.

The skilled artisan will be able to determine the amount of inhibitor which is to be administered to a human or animal. The amount of PTK inhibitor that is administered to an individual or animal will depend on a number of factors including the general health, size, age, and sex of the individual or animal and the route of administration. It will also depend on the degree, location and severity of the individual's or animal's osteoarthritis or cartilage degradation. One of ordinary skill in the art will be able to determine the precise dosage according to these and other factors. Typically, between about 0.1 mg per day and about 1000 mg per day are administered to the individual. Preferably, between about 0.1 mg per day and about 100 mg per day are administered to the individual, more preferably between about 1 mg per day and about 30 mg per day. The amount of PTK inhibitor administered to an animal will also depend on the type of animal.

The inhibitor can be administered intraarticularly (for example by injection) into a joint with cartilage degradation caused by osteoarthritis. Intra-articular injection has the advantage that the inhibitor is localized to the site of injection and that the concentration of inhibitor in other parts of the body is reduced. This is particularly advantageous in reducing undesirable side-effects when the protein tyrosine kinase inhibitor used to treat osteoarthritis or reduce cartilage degradation is non-specific and inhibits other protein kinases. Other modes of parenteral administration which can be used include systemic administration, such as by intramuscular, intravenous, subcutaneous, or intraperitoneal injection.

In a preferred embodiment, the inhibitor can be administered orally, for example, in capsules, suspensions or tablets. Alternatively, the inhibitor can be administered topically near the joint with cartilage degradation caused by osteoarthritis.

The PTK inhibitor can be administered to the individual or animal in conjunction with an acceptable pharmaceutical carrier as part of a pharmaceutical composition for treating osteoarthritis. Suitable pharmaceutical carriers may contain inert ingredients which do not interact with the PTK inhibitor. Standard pharmaceutical formulation techniques may be employed such as those described in Remington's Pharmaceutical Sciences, Mack Publishing Company, Easton, Pa. Suitable pharmaceutical carriers for intraarticular and other parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). Suitable carriers for topical administration include commercially available inert gels, liquids supplemented with albumin, methyl cellulose or a collagen matrix. Typical of such formulation are ointments, creams and gels. Preferred carriers for topical administration are those which facilitate penetration of the skin by the PTK inhibitor.

The PTK inhibitor can also be administered as at least one physiologically acceptable salt, such as, the hydrochloride salt, the hydrobromide salt and acetic acid salt.

In another embodiment of the present invention the composition, in addition to the inhibitor, additionally comprises one or more pharmacologically active agent. Osteoarthritis is characterized by pain in the afflicted joints. Consequently, it can be advantageous to administer the PTK inhibitor with an analgesic or other pain-killing medication. Suitable analgesics include acetyl salicylic acid, acetominophen, and the like.

Osteoarthritis can be characterized by inflammation in the afflicted joints. Consequently, it may also be advantageous to administer the PTK inhibitor together with an anti-inflammatory agent such as a non-steroidal anti-inflammatory drug or steroid (e.g. triamcinolone, amcinodide, and the like). Osteoarthritis is also characterized by over-activity of matrix metalloproteinase enzymes. Consequently, it may also advantageous to co-administer the PTK inhibitor with a matrix metalloproteinase inhibitor.

The invention will now be further and specifically described by the following examples.

EXEMPLIFICATION

Example 1

Inhibition of Cartilage Degradation by Protein Tyrosine Kinases Inhibitors in a Chondrocyte Cell Culture Matrix Breakdown Assay Isolation of the Cartilage A cell culture assay was used to measure the ability of the test compounds to slow the degradation of the extracellular matrix by a metalloproteinase. This assay measured the amount $^{35}$S released from chondrocytes grown in a media with $^{35}$S labeled sodium sulfate. The cell culture assay was carried out as follows:

Two or three 1 to 3 week old calf joints were obtained from an abattoir. The proximal end of the shank was about 4–5' long to facilitate immobilization in the holder. The joint was kept cool and transported on ice. The exterior of the intact joints was washed well with a suitable anti-microbial soap, rinsed clean with warm water, rinsed in betadine and then finally rinsed with 70% ethanol. Up to this point all steps were done in a manner to ensure that the joint was kept as clean as possible. All subsequent steps were performed in a sterile field (i.e., in a Edgeguard laminar flow tissue culture hood). The joint was immobilized and the synovial fluid was aspirated with a needle and syringe. The joint was then cut open to expose the articular cartilage using a #21 scalpel. Using locking hemostats, forceps and a #15 scalpel, the cartilage was excised in full thickness pieces. Care was taken not to cut too deep into the subchondral bone to prevent bleeding. The cartilage pieces were placed into a 50 mL centrifuge tube containing 25 mL of Delbecco's phosphate buffered saline (D-PBS) supplemented with 1% antibiotic solution (penicillin, streptomycin and fungizone; GIBCO/BRL). The slices from each joint were then placed into separate 50 mL centrifuge tubes. The D-PBS was decanted and replaced with 25 mL of fresh D-PBS supplemented with antibiotics and subsequently agitated gently.

Enzymatic Digestion

The cartilage pieces were transferred to a fresh 50 mL centrifuge tube and rinsed once more with 25 mL of D-PBS minus antibiotics. An enzymatic digestion solution containing 1 mg/mL of hyaluronidase in serum-free 1:1 DMEM/Ham's F-12 (DMEM/F12) was prepared. This solution was filter sterilized with 0.22 mm Milex-GV filter and kept on ice until ready to use. The cartilage pieces were digested with approximately 5 mL of hyaluronidase solution per joint for 2×15 minutes at 37° C. in the 50 mL centrifuge tube with gentle agitation at the 15 minute mark. This procedure removed residual hyaluronic acid from the surface of the chips. The enzymatic digestion solution was then aspirated and the cartilage pieces were rinsed with 25 mL of D-PBS.

A second enzymatic digestion solution containing 2.5 mg trypsin and 2 mg collagenase P per mL serum-free DMEM/F12 was prepared. This solution was also filter sterilized with a 0.22 mm Millex-GV filter and kept on ice until ready to use. The cartilage pieces were digested with approximately 5 mL of trypsin: collagenase solution per joint for 2×15 minutes at 37° C. in the 50 mL centrifuge tube with gentle agitation at the 15 minute mark. This procedure removed the synovial fibroblasts and any adherent connective tissue from the surface of the chips. The enzymatic digestion solution was then carefully removed and saved and the cartilage pieces were rinsed with 25 mL of D-PBS.

A third enzymatic solution containing 2 mgs of collagenase P (BMB) per mL serum-free DMEM/F12 was prepared. This solution was filter sterilized with a 0.22 mm Millex-GV filter and kept on ice until ready to use. The pre-digested cartilage pieces were finally digested with approximately 20 mL of enzymatic digestion solution per joint for 5–6 hours at 37° C. in a Bellco stirring digestion flask, at which point the cartilage was fully digested away.

Culture and Growth of Isolated Chondrocytes

The enzymes in the synovial fibroblast and chondrocyte digest were neutralized by addition of an equal volume of DMEM/F12 supplemented with 5% fetal bovine serum. Fibroblasts were plated in DMEM at a cellular density of $6.6 \times 10^3$ cells per $cm^2$. The chondrocytes were recovered by filtration through a 70 mm nylon Cell Strainer (Falcon Labware, Inc.), which removed the remaining undigested tissue pieces and clumps of cells. Chondrocytes were then collected by centrifugation at 1000×g for 10 minutes at room temperature. The chondrocytes were then resuspended in 40 mL of DMEM/F12 supplemented with 5% fetal bovine serum. A 200 µL aliquot in 20 mL of isoton was quantitated in a Coulter counter. Chondrocytes were diluted with 1:1 (v/v) DMEM/F-12 supplemented with 5% fetal bovine serum to a density of $2 \times 10^4$ cells per $cm^2$ of culture surface. This density allowed the cells to be at confluence as soon as they are plated. Four days later the cells were again fed with media. This time period ensured the attachment of the chondrocytes to the plastic well.

Chondrocytes were plated at $8 \times 10^4$ cells/2 $cm^2$ per well with 0.5 mL of 1:1 (v/v) DMEM/F12 supplemented with 10% fetal bovine serum in 24 well plates and incubated for 4 days. The cultures were then fed on days 4, 7, 11, 14, 18 and 21 with 0.5 mL/well of DMEM/F12 plus 10% fetal bovine serum. At this time the cells were densely confluent and have developed a three-dimensional extracellular matrix.

Radiolabel & Chase of Chondrocytes

On day 22, the wells are rinsed 2×1 mL with D-PBS and incubated for 30 minutes in 0.5 mL of DMEM/F12 per well. This starve media was removed, replaced with 0.5 mL/well of DMEM/F23 plus 10 µCi $^{35}$S labeled sodium sulfate per well and incubated for 48 hours at 37° C. On day 24, the labeling media is removed. The wells were then re-fed with 0.5 mL of DMEM/F12 plus 10% fetal bovine serum. The cultures were "chased" with cold sulfate (in the tissue culture media) for two more days and on day 26 were re-fed with 0.5 mL of fresh DMEM/F12 plus 10% fetal bovine serum.

Experimental Addition and Harvest

On day 27, the wells were rinsed 2×1 mL with D-PBS and incubated for 22–24 hours with 0.5 mL/well of serum free DMEM/F12, 1 ng/ml of rhIL-1α, plus the compound being tested at the desired concentrations. The wells were carefully rinsed to remove any residual fetal bovine serum which could affect the final results. A first control was run in which the assay was carried out in the absence of the compound being tested. A second control was also run in which the assay was carried out in the absence of test compound and rhIL-1α. On day 28 the 0.5 mL of media was removed and counted in a mini-vial with 4 mL of scintillation fluid. The cell layer was rinsed 1×1 mL with D-PBS and harvested with 0.5 mL of 1×trypsin-EDTA (purchased from Gibco-BRC, Life Technologies, Gaithersburg, Md.) (incubated for at least 15–20 minutes) for scintillation counting as before. The data is expressed as percent radiolabel released in the media of the total according to the formula:

$$\% \text{ release} = \frac{cpm_{media}}{(cpm_{media}) + (cpm_{cell\ layer})}$$

The average percent release is used to determine a percent inhibition according to the following formula:

$$\% \text{ Inhibition} = \frac{A - B}{C - B} \times 100,$$

wherein,
A=% release in presence of test compound;
B=% release in control; and
C=% release in presence of rhIL-1α.

Kinase inhibitors that were examined in this experiment were 10 µM Herbimycin A (PTK inhibitor), 50 µM Genistein (PTK inhibitor), 5 µM H88 (protein kinase A inhibitor, hereinafter "PKA" inhibitor), 0.5 µM H89 (PKA inhibitor), 0.5 µM Calphostin C (protein kinase C inhibitor, hereinafter "PKC" inhibitor), 1 µM Chelerythrine (PKC inhibitor), and 5 µM KN-93 (Ca/Calmodulin-dependent kinase II inhibitor). Only the tyrosine kinase inhibitors Herbimycin A and Genistein had any inhibitory effect on the IL-1 induced release of $^{35}$S-labelled proteoglycans, with the inhibitory effect ranging from 75% to 100%. PKC, PKA, and Calcium/Calmodulin-dependent kinase II inhibitors had no effect.

The assay described above was repeated. Genistein and Herbimycin A showed 58% and 89% inhibition, respectively. Little or no inhibition was observed with the above PKA, PKC, PKG, (0.5 µM H89) and Calcium/calmodulin-dependent protein kinase II inhibitors. The casein kinase I inhibitor CKI-7 (20 µM) also showed no inhibition. Of additional note is the fact that several tyrphostins (tyrosine kinase inhibitors) were also tested in this assay. The concentration and percent inhibition were as follows: 50 µM Tyrphostin AG 82 (40% inhibition), 50 µM Tyrphostin AG 126 (no inhibition), 50 µM Tyrphostin AG 556 (100% inhibition), 1 µM Tyrphostin AG 1296 (no inhibition), and DAPH at 2 µM (no inhibition) and 20 µM (no inhibition).

Example 2

Inhibition of Cartilage Degradation in the Bovin Cartilage Explant Assay by Protein Tyrosine Kinase Inhibitors A tissue culture assay was used to measure the ability of the compounds of the present invention to slow the degradation of the extracellular matrix by metalloproteinases. This assay measured the amount of $^{35}$S-glycosaminoglycan ($^{35}$S-GAG) released from labeled bovine cartilage explants.

Knee joints from a 1 to 3 week old calf were obtained immediately after sacrifice from the Abattoir and then transported on ice. The intact joints were washed well with tap water and soaked in 50% (v/v) Povidine iodine solution, obtained from Burre National, Inc., Baltimore, Md. All subsequent steps were performed in a laminar flow tissue culture hood using standard sterile technique. The joint was immobilized in a shank holder and the joint capsule was cut open to expose the articular cartilage. Cartilage explant plugs, approximately 15 mg wet weight, were removed from the flat articulating surfaces in the lower-most region of the knee joint using a sterile steel cork-borer and collected in a 250 mL roller bottle containing about 100 mL fresh Delbecco's minimum essential medium (DMEM), obtained from Gibco BRC, Life Technologies, Gaithersburg, Md., containing 4.5 g/l (D)-glucose and (L)-glutamine, without sodium pyruvate. The fresh media also contained enough Hepes buffer and sodium bicarbonate such that the pH was about 7.4. The media was then further supplemented just before use with 100 units Penicillin, 100 µg Streptomycin, and 50 µg (L)-ascorbic acid per mL of medium.

Once collected, the explant plugs were washed four times with 50 mL fresh DMEM. The plugs were then placed in the incubator for a minimum of 1 hour to equilibrate, before proceeding to make disks from the articulating surface of each plug. A 1 mm thick disk was sliced from individual plugs from the end that was the articulating surface of the joint. The plug was held steady in the sterile template (4 mm diameter ×1.5 mm deep) using sterile forceps. A scalpel blade was used to carefully slice off the disk. Only the superficial articulating surface responded well in culture.

Individual disks obtained were transferred to a tissue culture flask containing about 100 mL fresh media. The flask containing the disks was placed in an incubator at 37° C. (with 5% $CO_2$, 95% air) and allowed to equilibrate overnight and at least one additional day before labeling. When ready to label, the old media was replaced with 50 mL fresh media containing about 1.2 mCi $^{35}$S-Sodium Sulfate. The plugs were labeled in bulk for about 48 hours. The next morning, the "hot" media was removed and replaced with fresh "cold" media. The disks were again allowed to equilibrate overnight before being used for actual experiments.

The media in which the disks were stored was changed immediately prior to performing the assay. The disks were then returned to the incubator until the test media and the two control media had been prepared. The test media consisted of the desired concentration of a compound being tested for its ability to inhibit extracellular matrix degradation, concomitant recombinant human Interleukin rhIL-1α (5 ng/mL) in fresh DMEM solution and plasminogen (0.4 µM). The control media were identical to the test media, except that the first control media lacked rhIL-1α and the second control media lacked the test compound. 250 µL of each of the test and control media were transferred to separate 96-well TC plates. Flamed forceps were used to transfer a disk from the incubator to each 96-well TC plates that had been filled with either the test media or one of the two control media.

The TC plates were then placed in the incubator and cultured for 3–4 days (initial incubation with rhIL-1α alpha takes at least 3 days to stimulate endogenous metalloproteinases). A 50 µL aliquot of media from each TC plate was saved and counted. The rest of the media was removed with a suction device.

The cartilage disks from each TC plate were also saved for counting. The disks were removed with forceps and placed in eppendorf tubes and then digested with papain at 50–55° C. for 4–6 hours. A 50 µM aliquot was then counted.

The percent $^{35}$S-GAG release is calculated as follows:

$$\% \ ^{35}\text{S-GAG release} = \{(cpm_{medium})/(cpm_{medium} + cpm_{explant})\} \times 100\%$$

The percent inhibition at 50 µM of extracellular matrix damage in cartilage explant was calculated as follows:

$$\% \ \text{Inhibition} = \frac{(A-B)-(C-B)}{(A-B)} \times 100,$$

wherein
A=% GAG release induced by rhIL-1α;
B=% GAG release in the absence of rhIL-1α; and
C=% GAG release in the presence of rhIL-1α plus 50 µM of compound being tested.

The following protein kinase inhibitors were tested in the assay described above:

| INHIBITORS | SPECIFICITY | CONCENTRATION |
| --- | --- | --- |
| Calphostin C | Protein Kinase C Inhibitor | 2.0 µm |
| Chelerythrine | Protein Kinase C Inhibitor | 10.0 µm |
| H-88 | Protein Kinase A Inhibitor | 10.0 µm |
| H-89 | Protein Kinase A Inhibitor | 10.0 µm |
| KN-93 | Calcium/Calmodulin Dependent Kinase II Inhibitor | 2.0 µm |
| Herbimycin A | Protein Tyrosine Kinase Inhibitor | 2.0 µm |

The assay with Herbimycin A (2µM) (a tyrosine kinase inhibitor) showed about about 70% inhibition of the IL-1-stimulated release of radiolabelled proteoglycan. None of the other protein kinase inhibitors showed any significant inhibition of proteoglycan release. This result shows that protein tyrosine kinase inhibitors can reduce IL-1 induced matrix metalloproteinase (MMP) activity. See Example 3 for a more detailed discussion on the role of IL-1 and plasminogen on MMP activity.

Example 3

Inhibition by Protein Tyrosine Kinase Inhibitors of IL-1-Induced Aggrecanase Degradation of $^{35}$Sulfate Labelled Proteoglycan in Bovine Cartilage Explants The assay described in Example 2 can be carried out with and without added plasminogen. With plasminogen, the active forms of the metalloproteinases (MMPs) and plasmin were generated. It is believed that MMPs, "aggrecanase" and plasmin degraded the cartilage explant in this assay. Without added plasminogen, Western blot data suggested that only the inactive pro-forms of the MMPs were produced. Therefore, in the absence of plasminogen, cartilage degradation occurred primarily as a result of "aggrecanase" activity.

To test for aggrecanase activity, the assay described in Example 2 was performed in the absence of added plasminogen with the following tyrosine kinase inhibitors: (genistein (50μM) and herbimycin A (1 μM). Genistein showed a 37% inhibition while herbimycin A showed a 78% inhibition.

A dose response was performed for herbimycin A. The results show that 0.25 μM, 0.5 μM and 1.0 μM herbimycin A inhibit the release of $^{35}$S-labelled proteoglycan in a does-dependant fashion: 55%, 63% and 78%, respectively.

In a final experiment, two tryphostins (tyrosin kinase inhibitors) were also tested in the bovine explant assay described above: 50 μM tyrphostin AG 82 and 50 μM tyrphostin AG 126. A 31% inhibition was observed for tyrphostin AG 82, while no effect was seen for tyrphostin AG 126.

These results indicate that tyrosine kinase inhibitors can inhibit IL-1-induced aggrecanase activity and the cartilage degradation resulting from IL-1 induced aggrecanase activity.

Example 4

Inhibition of IL-1-Induced Increases in Stromelysin MRNA Levels in Primary Bovine Chondrocytes by Protein Tyrosine Kinase Inhibitors The isolation of cartilage and the enzymatic degradation of cartilage was carried out as described in Example 1.

Chondrocytes were recovered by addition of an equal volume of DMEM/F12 supplemented with 10% fetal bovine serum (FBS) to neutralize enzymes, filtration through a 70μm nylon Cell Strainer (Falcon), and centrifugation at 1000×g for ten minutes at room temperature. Chondrocytes were seeded in T-150 plates at 5×10$^4$ cells/cm$^2$ using 1:1 DMEM/F12, 10% FBS, 1% antibiotic solution (penicillin, streptomycin, fungizone: GIBCO/BRL), and incubated at 37° C., 5% $CO_2$. Cells were refed with DMEM/F12 plus 10% FBS on days 4, 7, and 10. On day 11, test cultures (except for the+interleukin 1α control) were rinsed in phosphate buffered saline (PBS), and preincubated for 2 hours with 5 ml of serum-free DMEM/F12 containing one of the following protein kinase inhibitors:
1) Protein kinase A (PKA) inhibitors; 0.5 μM H88 (Seikagaku Corp.), 0.5 μMH89 (Seikagaku Corp.); 2) Protein kinase G (PKG) and PKA inhibitor; 5.0 μM H89;

3) Protein kinase C. (PKC) inhibitors; 0.5 μM Calphostin C (Calbiochem), 1.0 μM chelerythrine (Calbiochem); 4) $Ca^{2+}$/Calmodulin Kinase II inhibitor; 5.0 μM KN93 (Seikagaku Corp.); 5) Protein tyrosine kinase (PTK) inhibitors; 50 μM Genistein (Calbiochem), 10 μM Herbimycin A (Calbiochem), 50 μM Tyrphostin A25 (AG 82) (Calbiochem), 50 μm Tyrphostin AG 126 (Calbiochem), 50 μM Tyrphostin B56 (AG 556) (Calbiochem), 20 μM DAPH (Calbiochem).

Recombinant human interleukin 1 α (IL-1α) (R & D Systems) at 1 ng/ml was then added to all cultures (except the IL-1α control) for 24 hours in serum-free DMEM/F12 containing 1% antibiotic solution.

RNA STAT 60 (Tel-Test "B", Inc.) was used to extract total RNA from the cell layer following manufacturer's suggested protocol. 15 μg of total RNA from each condition above was separated in a 2.2M formaldehyde/1.2% agarose gel, and transferred to a nylon support membrane (Schleicher & Schuell) by mild alkaline transfer using the TURBOBLOTTER™ system and the manufacturer's suggested protocol (Schleicher & Schuell). RNA on the Northern blot was fixed to the membrane by baking at 80° C. for 30 minutes.

DNA probes for human stromelysin and human glyceraldehyde-6-phosphate dehydrogenase (GAPDH) were labelled with [α-$^{32}$p]dCTP (Amersham) using the Random Priming Kit (Boehringer Mannheim) and the manufacturer's suggested protocol.

Prehybridization (1.5 hours) and hybridization (overnight) of the Northern blot with the radioactive probes were performed in 50% formamide, 1×GIBCO/BRL hybridization solution, 0.1% SDS, and 10mM monobasic sodium phosphate, at 42° C. The blot was successively washed two times in 1×SSC/0.1% SDS (15 minutes/wash at room temperature), and two times in 0.2×SSC/0.1% SDS (30 minutes/wash at 55° C.). The blot was allowed to air dry, and was exposed to X-ray film, with intensifying screen, overnight at −70° C.

The results of the Northern blot experiment demonstrate dramatically that the tyrosine kinase inhibitors Genistein, Herbimycin A, Tyrphostin B56 (AG 556), and DAPH were able to inhibit the IL-1-induced upregulation of stromelysin mRNA levels. Total inhibition of IL-1-induced upregulation of stromelysin MRNA occurred when the tyrosine kinase inhibitors were used. None of the pKA, PKC, PKG, or $Ca^{2+}$/Calmodulin Kinase II inhibitors were able to demonstrate any efficacy, as no reduction in stromelysin mRNA levels were seen when compared with the levels in IL-1-treated chondrocytes. In addition, the two tyrosine kinase inhibitors Tryphostin A25 (AG 82) and Tyrphostin AG 126 had no effect on IL-1-induced stromelysin mRNA levels indicating a specificity requirement within protein tyrosine kinase inhibitors.

Example 5

Inhibition of IL-1 Induced Increase in Prostromelysin Protein Levels in Primary Bovine Chonodrocytes by Protein Tyrosine Kinase Inhibitors Isolation and culturing of primary bovine articular chondrocytes, as well as addition of inhibitors were performed as indicated above in Example 4. The following protein kinase inhibitors were tested: 1) Protein kinase A (PKA) inhibitors; 0.5 μM H88 (Seikagaku Corp.), 0.5 μM H89 (Seikagaku Corp.), 2) Protein kinase C (PKC) inhibitors; 0.5 μM Calphostin C (Calbiochem), 1.0 μM Chelerythrine (Calbiochem); 3) $Ca^{2+}$/Calmodulin Kinase II inhibitor; 5.0 μM KN93 (Seikagaku Corp.); 4) Protein tyrosine kinase (PTK) inhibitors; 50 μM Genistein (Calbiochem), 10 μM Herbimycin A (Calbiochem).

After the 24 hour IL-1α incubation, the media of each sample was measured and collected on ice in the presence of the protease inhibitors EGTA (5 mM), Pefabloc (1 mM), pepstatin (1 μg/ml), and NEM (5 mM). Media were concentrated approximately 40 fold using a Centriprep-10 ultrafiltration device (Amicon). Concentrated samples were normalized to equivalent starting concentrations (cell number/culture volume), were reduced in the presence of SDS Laemmli sample buffer and electrophoresed in a precast 12% polyacrylamide gel (BioRad). Protein samples were then electroblotted to nitrocellulose and immunodetected using a primary antibody that recognizes both prostromelysin and stromelysin. Immunoreactive bands were visualized with the ABC detection (Pierce) and an NBT/BCIP color reagent (Sigma).

Prostromelysin was detected in the presence of IL-1α as expected. No prostromelysin was detected in the absence of IL-1 treatment. Furthermore, the control experiment revealed that none of the inhibitors had an effect on prostromelysin levels in the absence of IL-1α.

The inhibitors H-88 and H-89 (specific for PKA) calphostin C (specific for PKC) and KN-93 (specific for calcium/calmodulin-dependent protein kinase II) showed no effect on the Il-1-induced prostromelysin levels. In contrast, Il-1-induced prostromelysin expression was completely inhibited by both of the specific tyrosine kinase inhibitors, genistein and herbimycin A.

A repeat of the Western immunoblotting experiment using antistromelysin antibodies was performed. Furthermore, additional inhibitors from four enzyme families were examined: 1) Protein tyrosine kinase (PTK) inhibitors: 1 μM Tyrphostin AG 1296 (Calbiochem), 50 μM Tyrphostin A25 (AG 82) (Calbiochem), 50 μM Tyrphostin AG 126 (Calbiochem); 2) Guanylate cyclase inhibitor; 10 μM LY-83583 (Calbiochem); 3) Casein kinase I inhibitor; 20 μM CKI-7 (Seikagaku Corp.); and 4) Protein kinase G (PKG) and PKA inhibitor; 5.0 μM H89.

The results obtained for inhibitor effects on IL-1α-induced prostromelysin protein levels mirror those seen for stromelysin mRNA levels (see Example 4). PKC, PKA, PKG, and $Ca^{2+}$/Calmodulin Kinase II inhibitors had no effect on IL-1α-induced prostromelysin protein levels. Also, the tyrphostins AG 126, and AG 1296, the casein kinase I inhibitor CKI-7, and the guanylate cyclase inhibitor LY-83583 had no effect on IL-1α-induced prostromelysin protein levels. On the other hand, the tyrosine kinase inhibitors herbimycin A, genistein, tyrphostin AG 556, and DAPH demonstrated a dramatic reduction in prostromelysin protein levels. (It should be noted that DAPH generated immunoreactive bands that appeared to correspond to active forms of stromelysin by molecular weight.) tyrphostin AG 82 showed a slight inhibitory activity.

These results and the results reported in Example 4 suggest that tyrosine kinase inhibitors act, at least in part, by preventing the expression of matrix metalloproteinases (MMP) and/or the production of matrix metalloproteinase mRNA.

Example 6

Assessment of Genistein, Herbimycin A and Staurosporine in an in Vitro Cytotoxicity Assay The evaluation of cytotoxicity of compounds by in vitro methods allows one to establish criteria which allow rank ordering among compounds. These methods assess cell permeability, release of cytosolic enzymes, and oxidative potential of cells. The use of tetrazolium dyes to assess cytotoxicity has been established in the area of oncology, where such assays were developed to assess the cytotoxic potential of various chemotherapeutic agents. We have adapted the use of the MTT (3-(4,5-dimethylthiazol-2-yl)-2,5-diphenyl tetrazolium bromide) in an assay using primary bovine articular chondrocytes. The procedure for this assay is given below.

Chondrocytes are isolated from bovine calf radio-carpal joints as described in Example 1. Cells are plated in two 96-well plates at $4 \times 10^4$ cells per well, in DMEM/F12 media supplemented with 10% fetal bovine serum. The cultures are refed on days 4, 7, 11, 14, 18, 21 and 24. On day 27, the cells are rinsed with PBS, and incubated for 20 hours with 0.2 ml/well of serum-free DMEM/F12 plus 0.1% DMSO, and the test compounds. Genistein (50 μM), Herbimycin (10 μM) and Staurosporine (1 μM) were each used as test compounds. At 20 hours incubation, 50 μl of a 2 mg/ml MTT [3-(4,5-dimethylthazol-2-yl)-2,5-diphenyl tetraolium bromide] solution is added for 4 hours at 37° C. At 24 hours, the media is removed and the well rinsed once with 0.2 ml of PBS. 100 μl of mineral oil is then added to each well, and the plate incubated overnight at 40° C. The 96-well plate is then read in a microplate reader at 560 nm, with subtraction of absorbance at 750 nm to account for cell debris.

Thus Genestein and Herbimycin lacked any significant cytotoxicity (<50% reduction of MTT dye). Staurosporine displayed a reduction of MTT consistent with cytotoxicity and appeared to be cytotoxic to cultured chondrocytes over extended time periods.

Example 7

Effect of Protein Tyrosine Kinase Inhibitors on Aggrecan Degradation in Primary Bovine Articular Chondrocytes Primary bovine articular chondrocytes from calf adiocarpal joints were isolated and cultured as above in Example 1, up to and including the addition of the following protein kinase inhibitors: 1) Protein kinase A (PKA) inhibitors; 0.5 μM H88 (Seikagaku Corp.), 0.5 μM H89 (Seikagaku Corp.); 2) Protein kinase C (PKC) inhibitors; 0.5 μM Calphostin C (Calbiochem), 1.0 μM Chelerythrine (Calbiochem); 3) $Ca^{2+}$/Calmodulin Kinase II inhibitor; 5.0 μM KN93 (Seikagaku Corp.); 4) Protein tyrosine kinase (PTK) inhibitors; 50 μM Genistein (Calbiochem), 10 μM Herbimycin A (Calbiochem). After the 24 hour IL-1α incubation, the media of each sample was measured, and collected on ice in the presence of the protease inhibitors EGTA (5 mM), Pefaloc (1 mM), pepstatin (1 μg/ml), and NEM (5 mM). Media were concentrated approximately 40 fold using a Centriprep-10 ultrafiltration device (Amicon).

Proteoglycans contained within the media were deglycosylated by incubations with chondroitinase ABC, keratinase, and keratinase II following the procedure of Sandy et al. *J Biol Chem* (1991) 266:8683–8685 and Sandy et al. *J. Clin Invest* (1992) 89:1512–1516. Samples of deglycosylated media were subjected to 4–15% gradient SDS-PAGE and transferred to nitrocellulose membranes (2 ml-worth and 6 ml-worth of media were used for 2-B-6 and BC-3 immunoblotting, respectively.) The membranes were blocked with 1% nonfat dry milk and 1% BSA, and then incubated in either the BC-3 or 2-B-6 primary monoclonal antibody for 1 hour. The 2-B-6 antibody detects chondroitin sulfate stubs on chondroitinase-treated proteoglycans (both intact and degradation products. BC-3 antibody detects "ARGSV . . . ," the new N-terminus ("neoepitope") resulting from cleavage of aggrecan interglobular domain at $Glu^{373}/ALA^{374}$ by aggrecanase. It is of note to mention that the BC-3 and 2-B-6 antibodies were of low sensitivity. Following 3 washes, membranes were incubated in either alkaline phosphatase-conjugated goat anti-mouse (for the 2-B-6 blot) or biotinylated goat anti-mouse (for the BC-3 blot); followed by alkaline phosphatase-conjugated streptavidin/biotin complex). After washing 3 times, immunoreactive proteins were detected using NBT/BCIP (Sigma) colorimetric substrate.

The 2-B-6 antibody detected intact aggrecan (the uppermost band) and several aggrecan degradation products, along with decorin and biglycan (50K doublet), in the IL-1-treated media samples. The control sample (lacking IL-1) primarily shows intact aggrecan, and very faint degradation products. The bands in the IL-1 sample that are seen at 230K, 200K, 130K and 100K have been previously identified by sequence analysis to result from IL-1-induced "aggrecanase" cleavage.

Three major differences between the samples are noted. As expected, the total amount of PG fragments is increased with IL-1 vs. control (no IL-1 present). The intensity of a degradation fragment~230K is increased with IL-1 stimulation and has been shown to result from "aggrecanase" cleavage. The intensity of staining (i.e., total amount of PG fragments) is reduced in IL-1-stimulated chondrocytes treated with genistein and herbimycin A (tyrosine kinase inhibitors), relative to the H-88 and H-89 (PKA inhibitors), calphostin C and chelerythrine (PKC inhibitors), and KN-93 (calmodulin-dependent kinase inhibitor) samples. The effect of the tyrosine kinase inhibitors is consistent with results previously obtained for prostromelysin, both by Northern and Western analyses, in Examples 4 and 5.

In addition, treatment of IL-1-stimulated chondrocytes with genistein and herbimycin significantly reduce the level of the 230K aggrecan degradation product, while levels of the uppermost band (intact aggrecan) are increased, consistent with an inhibition of aggrecan degradation. In contrast, the samples with H-88, H-89, calphostin C, chelerythrine, and KN-93 show a pattern similar to IL-1 alone (i.e., roughly equal ratio of intact aggrecan to 230K fragment).

The BC-3 antibody detected an immunoreactive band at approximately 230K in IL-1-stimulated samples ±H-89 (PKA inhibitor) or calphostin C (PKC inhibitor), demonstrating aggrecanase degradative activity. In contrast, this aggrecanase-mediated fragment is not present in samples treated with the tyrosine kinase inhibitors, genistein and herbimycin A, consistent with the above 2-B-6 results. An inconsistency noted was the absence of this 230K band in the sample treated with KN-93 (calmodulin-dependent kinase inhibitor). No effect of this inhibitor has been observed in any of the previous studies (e.g., prostromelysin Western blotting, Northern blotting, and 2-B-6 above). The above BC-3 and 3B-6 data support the conclusion that inhibitors of PTKs inhibit IL-1-stimulated degradation of proteoglycan by aggrecanase.

A repeat of the Western immunoblotting experiment using 2-B-6 antibodies was performed. Furthermore, additional inhibitors from four enzyme families were examined: 1) Protein tyrosine kinase (PTK) inhibitors; 1 μM Tryphostin AG 1296 (Calbiochem), 50 μM Tyrphostin A25 (AG 82) (Calbiochem), 50 μM Tyrphostin AG 126 (Calbiochem), 50 μM Tyrphostin B56 (AG 556) (Calbiochem), 20 μM DAPH (Calbiochem); 2) Guanylate cyclase inhibitor; 10 μM LY-83583 (Calbiochem); 3) Casein kinase I inhibitor; 20 μM CKI-7 (Seikagaku Corp.); and 4) Protein kinase G (PKG) and PKA inhibitor; 5.0 μM H89.

As seen above, control media (no IL-1, no inhibitors) produced a major intact band of aggrecan. Also, once again none of the inhibitors for PKA, PKC, PKG, Calcium/calmodulin-dependent protein kinase II, or casein kinase showed any inhibition of IL-1-induced aggrecan degradation. In addition, the tyrphostins AG 126 and AG 1296 showed no inhibitory effect. On the other hand, inhibition of IL-1-induced aggrecan degradation was seen by herbimycin A (nearly 100% inhibition), tyrphostin AG 556 (100% inhibition), genistein (partial inhibition), DAPH (moderately strong inhibition), and tyrphostin AG 82 (moderate inhibition).

EQUIVALENTS

Those skilled in the art will know, or be able to ascertain using no more than routine experimentation, many equivalents to the specific embodiments of the invention described herein. These and all other equivalents are intended to be encompassed by the following claims.

What is claimed is:

1. A method of treating an individual or animal with osteoarthritis comprising administering to the individual or animal a therapeutically effective amount of a protein tyrosine kinase inhibitor, with the proviso that the protein tyrosine kinase inhibitor is not a flavone, isoflavone, hymenialdisine or hymenialdisine analogue.

2. The method of claim 1 wherein the protein tyrosine kinase inhibitor inhibits interleukin-1 stimulated cartilage degradation in chondrocytes in cell culture.

3. The method of claim 1 wherein the protein tyrosine kinase inhibitor inhibits interleukin-1 stimulated biosynthesis of matrix metalloproteinase enzymes in chondrocytes in cell culture.

4. The method of claim 2 wherein the protein tyrosine kinase inhibitor is represented by the following structural formula:

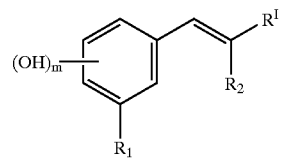

wherein:

m is one or two;

$R_1$ is —H, —OH or —OMe;

$R_2$ is —H or —CN; and $R^I$ is —H, —$NO_2$, halogen or an organic radical.

5. The method of claim 4 wherein the protein tyrosine kinase inhibitor is represented by the following structural formula:

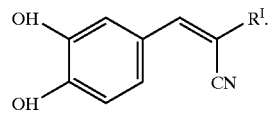

6. The method of claim 4 wherein the protein tyrosine kinase inhibitor is selected from the group consisting of tyrphostin AG 556 and tyrphostin AG82.

7. The method of claim 2 wherein the protein tyrosine kinase inhibitor is represented by the following structural formula:

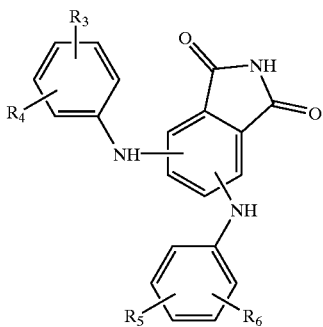

(II)

wherein $R_3$–$R_6$ are each independently selected from the group consisting of —H, —Cl, —OH and —OMe.

8. The method of claim 7 wherein the protein tyrosine kinase is 4,5-dianilinophthalimide (DAPH).

9. The method of claim 2 wherein the protein tyrosine kinase inhibitor is a compound represented by a structure selected from the group consisting of:

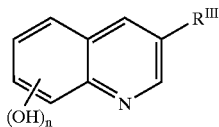

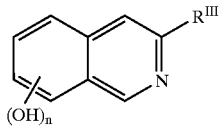

and

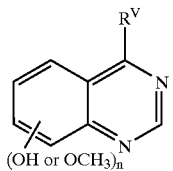

wherein:

n is one, two or three; and $R^{III}$ and $R^{V}$ are each an organic radical.

10. The method of claim 2 wherein the protein tyrosine kinase inhibitor is herbimycin A.

11. The method of claim 1 wherein the protein tyrosine kinase inhibitor inhibits interleukin-1 stimulated cartilage degradation in a cartilage explant assay.

12. The method of claim 2 wherein the protein tyrosine kinase inhibitor is represented by the following structural formula:

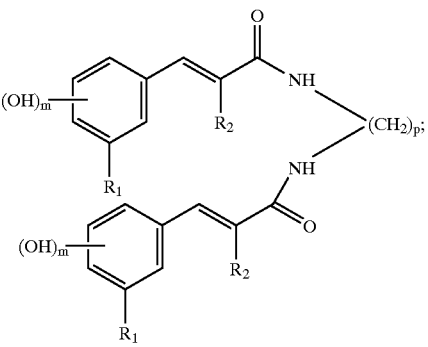

wherein:

m is one or two;

$R_1$ is selected from the group consisting of —H, —OH and —OMe;

$R_2$ is —H or —CN; and p is an integer from one to eight.

13. The method of claim 2 wherein the protein tyrosine kinase inhibitor is a tyrphostin.

14. The method of claim 1 wherein the protein tyrosine kinase inhibitor inhibits interleukin-1 stimulated aggrecanase activity by chondrocytes in cell culture.

* * * * *